US008880154B2

(12) United States Patent
Jones et al.

(10) Patent No.: US 8,880,154 B2
(45) Date of Patent: *Nov. 4, 2014

(54) FIBROUS MARKER AND INTRACORPOREAL DELIVERY THEREOF

(71) Applicant: SenoRx, Inc., Tempe, AZ (US)

(72) Inventors: Michael L. Jones, San Clemente, CA (US); Paul Lubock, Monarch Beach, CA (US); Lloyd H. Malchow, San Juan Capistrano, CA (US)

(73) Assignee: SenoRx, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/946,175

(22) Filed: Jul. 19, 2013

(65) Prior Publication Data
US 2013/0310686 A1    Nov. 21, 2013

Related U.S. Application Data

(63) Continuation of application No. 13/155,628, filed on Jun. 8, 2011, now Pat. No. 8,626,269, which is a continuation of application No. 10/444,770, filed on May 23, 2003, now Pat. No. 7,983,734.

(51) Int. Cl.
*A61B 17/00* (2006.01)
*A61B 19/00* (2006.01)

(52) U.S. Cl.
CPC ......... *A61B 19/54* (2013.01); *A61B 2019/5425* (2013.01); *A61B 17/0057* (2013.01); *A61B 2017/00637* (2013.01); *A61B 2017/00898* (2013.01); *A61B 2019/5408* (2013.01); *A61B 2019/5487* (2013.01)
USPC ............ 600/431; 600/414; 600/420; 600/426

(58) Field of Classification Search
USPC .................................. 600/420, 426, 431, 414
See application file for complete search history.

(56) References Cited

U.S. PATENT DOCUMENTS

| | | | |
|---|---|---|---|
| 2,481,408 A | 9/1949 | Fuller et al. | |
| 2,899,362 A | 8/1959 | Sieger, Jr. et al. | |

(Continued)

FOREIGN PATENT DOCUMENTS

| | | |
|---|---|---|
| DE | 1029528 B | 5/1958 |
| EP | 0146699 A1 | 7/1985 |

(Continued)

OTHER PUBLICATIONS

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

(Continued)

*Primary Examiner* — Peter Luong (57) ABSTRACT

An intracorporeal marker includes a fibrous unitary marker body having bioabsorbable fibers compressed into a compressed configuration, and bound in the compressed configuration by a polymer binding agent. The intracorporeal marker may be incorporated into an intracorporeal marker delivery device having a delivery cannula which has a distal tip, an inner lumen and a discharge opening in communication with the inner lumen. The compression and binding occur prior to insertion of the fibrous unitary marker body into the inner lumen of the delivery cannula. The fibrous unitary marker body is slidably disposed within and pushable through the inner lumen of the elongated delivery cannula proximal to the discharge opening.

20 Claims, 3 Drawing Sheets

(56) References Cited

U.S. PATENT DOCUMENTS

| | | |
|---|---|---|
| 2,907,327 A | 10/1959 | White |
| 3,005,457 A | 10/1961 | Millman |
| 3,128,744 A | 4/1964 | Jefferts et al. |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,820,545 A | 6/1974 | Jefferts |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,127,774 A | 11/1978 | Gillen |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,347,234 A | 8/1982 | Wahlig et al. |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,234 A | 8/1990 | Fujioka et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,018,530 A | 5/1991 | Rank et al. |
| 5,035,891 A | 7/1991 | Runkel et al. |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,234,426 A | 8/1993 | Rank et al. |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,100 A | 6/1994 | Herweck et al. |
| 5,320,613 A | 6/1994 | Houge et al. |
| 5,328,955 A | 7/1994 | Rhee et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,458,643 A | 10/1995 | Oka et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,545,180 A | 8/1996 | Le et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |

(56) References Cited

U.S. PATENT DOCUMENTS

| | | |
|---|---|---|
| 5,702,128 A | 12/1997 | Maxim et al. |
| 5,702,716 A | 12/1997 | Dunn et al. |
| 5,716,981 A | 2/1998 | Hunter et al. |
| 5,747,060 A | 5/1998 | Sackler et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,166,079 A | 12/2000 | Follen et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,419,621 B1 | 7/2002 | Sioshansi et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,447,524 B1 | 9/2002 | Knodel et al. |
| 6,447,527 B1 | 9/2002 | Thompson et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,544,231 B1 | 4/2003 | Palmer et al. |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |

(56) References Cited

U.S. PATENT DOCUMENTS

| | | |
|---|---|---|
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,626,899 B2 | 9/2003 | Houser et al. |
| 6,628,982 B1 | 9/2003 | Thomas et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,659,933 B2 | 12/2003 | Asano |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,881,226 B2 | 4/2005 | Corbitt, Jr. et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,958,044 B2 | 10/2005 | Burbank et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,135,978 B2 | 11/2006 | Gisselberg et al. |
| 7,160,258 B2 | 1/2007 | Imran et al. |
| 7,172,549 B2 | 2/2007 | Slater et al. |
| 7,189,206 B2 | 3/2007 | Quick et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,280,865 B2 | 10/2007 | Adler |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,329,414 B2 | 2/2008 | Fisher et al. |
| 7,407,054 B2 | 8/2008 | Seiler et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,565,191 B2 | 7/2009 | Burbank et al. |
| 7,569,065 B2 | 8/2009 | Chesbrough et al. |
| 7,637,948 B2 | 12/2009 | Corbitt, Jr. |
| 7,651,505 B2 | 1/2010 | Lubock et al. |
| 7,668,582 B2 | 2/2010 | Sirimanne et al. |
| 7,670,350 B2 | 3/2010 | Selis |
| 7,792,569 B2 | 9/2010 | Burbank et al. |
| 7,819,819 B2 | 10/2010 | Quick et al. |
| 7,819,820 B2 | 10/2010 | Field et al. |
| 7,871,438 B2 | 1/2011 | Corbitt, Jr. |
| 7,877,133 B2 | 1/2011 | Burbank et al. |
| 7,914,553 B2 | 3/2011 | Ferree |
| 7,983,734 B2 | 7/2011 | Jones et al. |
| 8,011,508 B2 | 9/2011 | Seiler et al. |
| 8,052,708 B2 | 11/2011 | Chesbrough et al. |
| 8,128,641 B2 | 3/2012 | Wardle |
| 8,157,862 B2 | 4/2012 | Corbitt, Jr. |
| 8,306,602 B2 | 11/2012 | Sirimanne et al. |
| 8,320,993 B2 | 11/2012 | Sirimanne et al. |
| 8,361,082 B2 | 1/2013 | Jones et al. |
| 8,579,931 B2 | 11/2013 | Chesbrough et al. |
| 8,626,270 B2 | 1/2014 | Burbank et al. |
| 2001/0003791 A1 | 6/2001 | Burbank et al. |
| 2001/0006616 A1 | 7/2001 | Leavitt et al. |
| 2001/0033867 A1 | 10/2001 | Ahern et al. |
| 2001/0049481 A1 | 12/2001 | Fulton, III et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0038087 A1 | 3/2002 | Burbank et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082517 A1 | 6/2002 | Klein |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0177776 A1 | 11/2002 | Crawford Kellar et al. |
| 2002/0188195 A1 | 12/2002 | Mills |
| 2002/0188196 A1 | 12/2002 | Burbank et al. |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0068312 A1 | 4/2004 | Sigg et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0116806 A1 | 6/2004 | Burbank et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0153074 A1 | 8/2004 | Bojarski et al. |
| 2004/0162574 A1 | 8/2004 | Viola |

(56) References Cited

U.S. PATENT DOCUMENTS

| | | |
|---|---|---|
| 2004/0167619 A1 | 8/2004 | Case et al. |
| 2004/0193044 A1 | 9/2004 | Burbank et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236211 A1 | 11/2004 | Burbank et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0063908 A1 | 3/2005 | Burbank et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0143656 A1 | 6/2005 | Burbank et al. |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0292690 A1 | 12/2006 | Liu et al. |
| 2007/0021642 A1 | 1/2007 | Lamoureux et al. |
| 2007/0057794 A1 | 3/2007 | Gisselberg et al. |
| 2007/0083132 A1 | 4/2007 | Sharrow |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0091120 A1 | 4/2008 | Fisher |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0131825 A1 | 5/2009 | Burbank et al. |
| 2009/0171198 A1 | 7/2009 | Jones et al. |
| 2009/0287078 A1 | 11/2009 | Burbank et al. |
| 2010/0010342 A1 | 1/2010 | Burbank et al. |
| 2010/0094169 A1 | 4/2010 | Lubock et al. |
| 2010/0198059 A1 | 8/2010 | Burbank et al. |
| 2010/0298698 A1 | 11/2010 | Burbank et al. |
| 2010/0324416 A1 | 12/2010 | Burbank et al. |
| 2011/0092815 A1 | 4/2011 | Burbank et al. |
| 2011/0184280 A1 | 7/2011 | Jones et al. |
| 2012/0078092 A1 | 3/2012 | Jones et al. |
| 2012/0116215 A1 | 5/2012 | Jones et al. |
| 2012/0179251 A1 | 7/2012 | Corbitt, Jr. |
| 2012/0215230 A1 | 8/2012 | Lubock et al. |
| 2013/0144157 A1 | 6/2013 | Jones et al. |
| 2013/0253315 A1 | 9/2013 | Burbank et al. |
| 2013/0281847 A1 | 10/2013 | Jones et al. |
| 2014/0058258 A1 | 2/2014 | Chesbrough et al. |
| 2014/0094698 A1 | 4/2014 | Burbank et al. |
| 2014/0114186 A1 | 4/2014 | Burbank et al. |

FOREIGN PATENT DOCUMENTS

| | | |
|---|---|---|
| EP | 0255123 A2 | 2/1988 |
| EP | 0292936 A2 | 11/1988 |
| EP | 0386936 A1 | 9/1990 |
| EP | 0458745 A1 | 11/1991 |
| EP | 0475077 A2 | 3/1992 |
| EP | 0481685 A1 | 4/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| FR | 2853521 A1 | 10/2004 |
| GB | 708148 | 4/1954 |
| JP | 2131757 A | 5/1990 |
| JP | 2006516468 A | 7/2006 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9608208 A1 | 3/1996 |
| WO | 9806346 A1 | 2/1998 |
| WO | 9908607 A1 | 2/1999 |
| WO | 9930764 A1 | 6/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0038579 A2 | 7/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 0241786 A2 | 5/2002 |
| WO | 03000308 A1 | 1/2003 |
| WO | 2004105444 A2 | 6/2004 |
| WO | 2004105626 A1 | 12/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

(56) References Cited

OTHER PUBLICATIONS

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large—Tissue Engineering", Biotechnol. Prog., vol. 14, No. 1, pp. 134-140, 1998.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From http://www.jnjgateway.com. 5 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

International Search Report for PCT/US2009/000945 mailed Jul. 16, 2009.

Written Opinion of the International Searching Authority for PCT/US2009/000945 mailed Jul. 16, 2009.

International Search Report for PCT/US2007/016902 mailed Feb. 28, 2008.

International Search Report for PCT/US2007/016902 mailed Feb. 4, 2009.

Written Opinion of the International Searching Authority for PCT/US2007/016902 mailed Feb. 4, 2009.

International Search Report for PCT/US2007016918 mailed Nov. 26, 2007.

Written Opinion of the International Searching Authority for PCT/US2007016918 mailed Feb. 4, 2009.

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.

FIBROUS MARKER AND INTRACORPOREAL DELIVERY THEREOF

CROSS-REFERENCE TO RELATED APPLICATIONS

This application is a continuation of U.S. patent application Ser. No. 13/155,628, filed Jun. 8, 2011, now U.S. Pat. No. 8,626,269, which is a continuation of U.S. patent application Ser. No. 10/444,770, filed May 23, 2003, now U.S. Pat. No. 7,983,734, entitled, "FIBROUS MARKER AND INTRACORPOREAL DELIVERY THEREOF".

FIELD OF THE INVENTION

The invention is directed generally to a fibrous marker and devices and systems for the intracorporeal delivery thereof to a target site within a patient.

BACKGROUND OF THE INVENTION

In diagnosing and treating certain medical conditions, it is often desirable to mark a suspicious body site for the subsequent taking of a biopsy, delivery of medicine, radiation, or other treatment, to mark a location from which a biopsy was taken, or at which some other procedure was performed. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a therapeutic plan for the appropriate surgical procedure or other course of treatment.

In many instances, the suspicious tissue to be sampled is located in a subcutaneous site, such as inside a human breast. To minimize surgical intrusion into a patient's body, it is often desirable to insert a small instrument, such as a biopsy needle, into the body for extracting the biopsy specimen while imaging the procedure using fluoroscopy, ultrasonic imaging, x-rays, magnetic resonance imaging (MRI) or any other suitable form of imaging technique. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

Periodic physical examination of the breasts and mammography are important for early detection of potentially cancerous lesions. In mammography, the breast is compressed between two plates while specialized x-ray images are taken. If an abnormal mass in the breast is found by physical examination or mammography, ultrasound may be used to determine whether the mass is a solid tumor or a fluid-filled cyst. Solid masses are usually subjected to some type of tissue biopsy to determine if the mass is cancerous.

If a solid mass or lesion is large enough to be palpable, a tissue specimen can be removed from the mass by a variety of techniques, including but not limited to open surgical biopsy, a technique known as Fine Needle Aspiration Biopsy (FNAB) and instruments characterized as "vacuum assisted large core biopsy devices".

If a solid mass of the breast is small and non-palpable (e.g., the type typically discovered through mammography), a biopsy procedure known as stereotactic needle biopsy may be used. In performing a stereotactic needle biopsy of a breast, the patient lies on a special biopsy table with her breast compressed between the plates of a mammography apparatus and two separate x-rays or digital video views are taken from two different points of view. With the assistance of a clinician, a computer calculates the exact position of the lesion in the breast. Thereafter, a mechanical stereotactic apparatus is programmed with the coordinates and depth information calculated by the computer and such apparatus is used to precisely advance the biopsy needle into the lesion. Depending on the type of biopsy needle(s) used, this stereotactic technique may be used to obtain histologic specimens e.g., obtained through coring needle biopsy or, more commonly, a biopsy with a vacuum assisted large core biopsy device. Usually at least five separate biopsy specimens are obtained at or around the lesion.

The available treatment options for cancerous lesions of the breast include various degrees of lumpectomy or mastectomy and radiation therapy, as well as chemotherapy and combinations of these treatments. However, radiographically visible tissue features, originally observed in a mammogram, may be removed, altered or obscured by the biopsy procedure, and may heal or otherwise become altered following the biopsy. In order for the surgeon or radiation oncologist to direct surgical or radiation treatment to the precise location of the breast lesion several days or weeks after the biopsy procedure was performed, it is desirable that a biopsy site marker be placed in or on the patient's body to serve as a landmark for subsequent location of the lesion site. A biopsy site marker may be a permanent marker (e.g., a metal marker visible under X-ray examination), or a temporary marker (e.g., a bioresorbable marker detectable with ultrasound). While current radiographic type markers may persist at the biopsy site, an additional mammography generally must be performed at the time of follow up treatment or surgery in order to locate the site of the previous surgery or biopsy. In addition, once the site of the previous procedure is located using mammography, the site must usually be marked with a location wire which has a hook on the end which is advanced into site of the previous procedure. The hook is meant to fix the tip of the location wire with respect to the site of the previous procedure so that the patient can then be removed from the confinement of the mammography apparatus and the follow-up procedure performed. However, as the patient is removed from the mammography apparatus, or otherwise transported the position of the location wire can change or shift in relation to the site of the previous procedure. This, in turn, can result in follow-up treatments being misdirected to an undesired portion of the patient's tissue.

As an alternative or adjunct to radiographic imaging, ultrasonic imaging and visualization techniques (herein abbreviated as "USI") can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are visible using USI. Such a marker enables a follow-up procedure to be performed without the need for traditional radiographic mammography imaging which, as discussed above, can be subject to inaccuracies as a result of shifting of the location wire as well as being tedious and uncomfortable for the patient.

Placement of a marker or multiple markers at a location within a patient's body requires delivery devices capable of holding markers within the device until the device is properly situated within a breast or other body location. Accordingly, devices and methods for retaining markers within a marker delivery device while allowing their expulsion from the devices at desired intracorporeal locations are desired.

SUMMARY OF THE INVENTION

The invention is directed to a fibrous, swellable marker which positions a long-term radiographically detectable marker element within a target site of a patient's body. Preferably, short term ultrasound detectable markers are also delivered into the target site along with the fibrous marker.

The fibrous marker embodying features of the invention is formed at least in part of a fibrous material, such as oxidized, regenerated cellulose, polylactic acid, a copolymer of polylactic acid and glycolic acid, polycaprolactone, in a felt and/or fabric or woven structure. The fibrous marker material is swellable in the presence of body fluid, such as blood or plasma, or other water based fluid. The fibrous material is formed into an elongated member and bound in a compressed condition to provide sufficient column strength to facilitate introduction into and discharge from a tubular delivery device. Suitable binding agents for holding the fibrous marker in a compressed condition are water soluble polymers such as polyvinyl alcohol, polyethylene glycol, polyvinyl pyrollidone. One or more radiographically detectable marker elements are provided with the fibrous marker, preferably centrally located, to ensure that the radiographically detectable element is disposed at a more or less central location within the target site rather than at a site margin.

The one or more short term ultrasonically detectable markers, which are preferably delivered with the fibrous markers, are formed of bioabsorbable materials. Details of suitable short term ultrasonically detectable markers can be found in U.S. Pat. No. 6,161,034, issued Dec. 12, 2000, U.S. Pat. No. 6,347,241, issued Feb. 12, 2002, application Ser. No. 09/717,909, filed Nov. 20, 2000, now U.S. Pat. No. 6,725,083, and application Ser. No. 10/124,757, filed Apr. 16, 2002, now U.S. Pat. No. 6,862,470. These patents and applications are assigned to the present assignee and are incorporated herein in their entirety by reference.

Marker delivery systems embodying features of the invention include an elongated cannula with an inner lumen extending therein and a discharge opening or port in a distal portion of the cannula which is in fluid communication with the inner lumen. The fibrous marker embodying features of the invention is slidably disposed within the inner lumen of the cannula, preferably along with at least one short term marker. The short term marker is preferably disposed distal to the fibrous marker so that upon discharge from the cannula into a target site cavity, the fibrous marker will swell upon contact with body fluids to block the accessing passageway. The discharge opening of the delivery device is preferably closed with a plug to hold in the markers during handling and delivery and to prevent tissue and fluid from entering the inner lumen through the discharge opening during delivery. Any water based fluid which may enter into the inner lumen of the delivery device can result in the expansion or swelling of the marker bodies within the inner lumen and prevent their deployment. Preferably, the plug is formed of a water swellable material, so that the plug occludes the opening upon contact with a water based fluid and thereby prevents the premature expansion of the markers within the inner lumen. The plug is easily pushed out of the discharge opening of the tubular delivery device.

A movable plunger is slidably disposed within the inner lumen of the delivery cannula from an initial position accommodating the marker or markers and the plug within the tube, to a delivery position to push a marker against the plug to push the plug out of the discharge opening and to then eject one or more markers through the opening into the target tissue site.

Upon being discharged into the intracorporeal target site, the fibrous marker swells on contact with body fluid, e.g. blood. The expanded fibrous marker fills or partially fills the cavity at the target site, positioning the radiopaque marker element within the interior of the target cavity. Additionally, a therapeutic agent, a diagnostic agent or other bioactive agent may be incorporated into the fibrous marker body. Such agents include a hemostatic agent to accelerate thrombus formation within the target cavity, an anesthetic agent, a coloring agent, an antibiotic agent, an antifungal agent, an antiviral agent, a chemotherapeutic agent, a radioactive agent and the like.

The plug secures the discharge opening on the distal portion of the cannula, but it is easily ejected or removed from the orifice, allowing the delivery of the markers to a desired site within a patient's body. The plug or the cannula itself may have retaining features, such as recesses, protuberances, detents and the like which are configured to releasably retain the plug or the short term markers proximal to the plug until ejection of the plug from the delivery tube is desired. The retaining features may be complementary pairs, such as a plug protuberance configured to fit into a recess in the cannula interior. For further plug details see application Ser. No. 10/174,401, filed on Jun. 17, 2002, now U.S. Pat. No. 7,651,505, entitled Plugged Tip Delivery Tube For Marker Placement. This application is assigned to the present assignee and is incorporated herein in its entirety by reference.

The invention, in one form thereof, is directed to an intracorporeal marker including a fibrous unitary marker body having bioabsorbable fibers compressed into a compressed configuration, and bound in the compressed configuration by a polymer binding agent.

The invention, in another form thereof, is directed to an intracorporeal marker comprising a fibrous unitary marker body configured as a roll of bioabsorbable fiber material having at least one wrap.

The invention, in another form thereof, is directed to an intracorporeal marker delivery device. The intracorporeal marker delivery device includes a delivery cannula which has a distal tip, an inner lumen and a discharge opening in communication with the inner lumen. A fibrous unitary marker body includes bioabsorbable fibers compressed into a compressed configuration and bound in the compressed configuration by a binding agent prior to insertion into the inner lumen of the delivery cannula. The fibrous unitary marker body is slidably disposed within and pushable through the inner lumen of the elongated delivery cannula proximal to the discharge opening.

The invention provides the advantages of a relatively long term fibrous marker which is easily deployed into a target site and which positions a permanent radiographically detectable marker element within a central portion of the target site. When combined with short term ultrasound markers, the target site is easily detected at a later date by personnel with minimal training. These and other advantages of the invention will become more apparent from the following description when taken in conjunction with the accompanying drawings.

DETAILED DESCRIPTION OF THE INVENTION

Figure 1A:
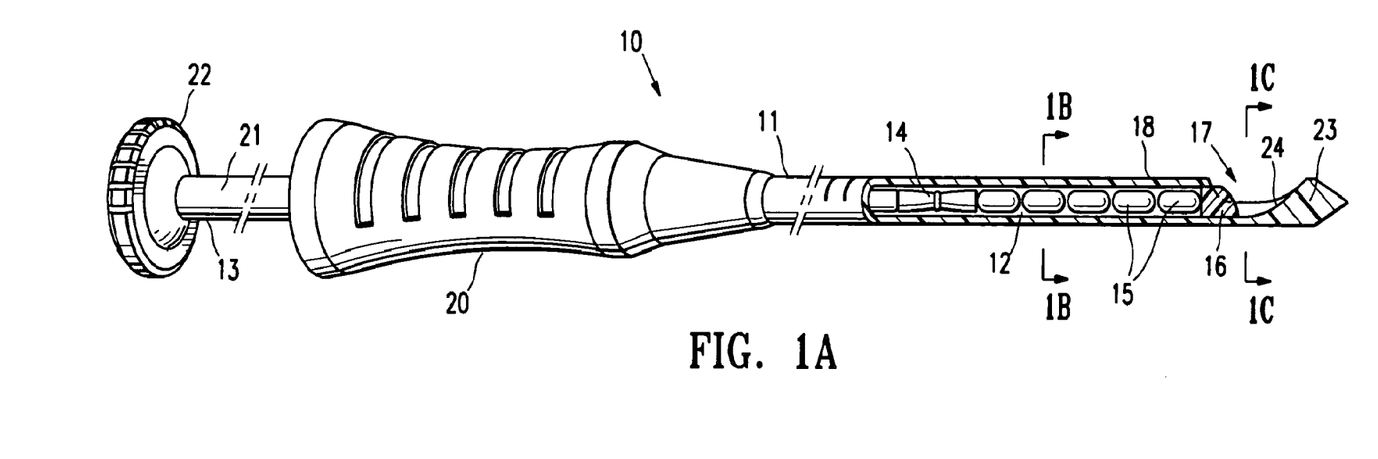
FIG. 1A is a partly cut-away perspective view of a marker delivery assembly showing a fibrous marker embodying features of the invention and several short term markers within a marker delivery device and a plug embodying occluding the discharge opening of the delivery device.
Figure 1B:
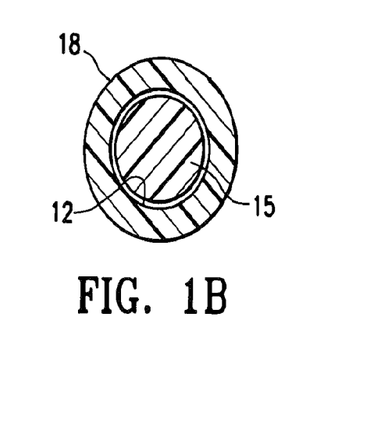
FIG. 1B is a transverse cross-sectional view of the marker delivery assembly of FIG. 1A taken at line 1B-1B.
Figure 1C:
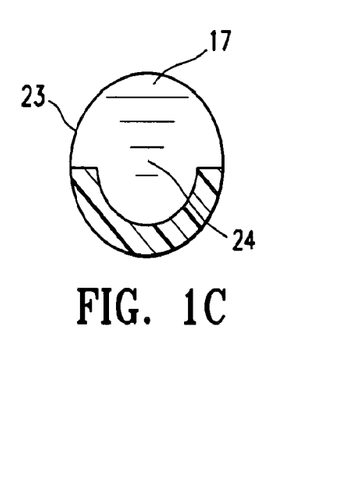
FIG. 1C is a transverse cross-sectional view of the marker delivery assembly of FIG. 1A taken at line 1C-1C.

A marker delivery assembly 10 embodying features of the invention and illustrated in FIGS. 1A-1C, includes a marker delivery cannula 11 which has an inner lumen 12, a plunger 13 slidably disposed within the inner lumen 12, a fibrous marker 14 and a plurality of short term ultrasonically detectable markers 15 slidably disposed within the inner lumen, and a plug 16 occluding a discharge opening 17 in the distal portion of the cannula 11. The delivery cannula 11 has an elongated shaft 18 which defines at least in part the inner lumen 12 and has a handle 20 on the proximal end of the cannula shaft 18 to facilitate handling and advancement of the device. The plunger 13 has a plunger shaft 21 and a plunger handle 22 to facilitate advancement of the plunger shaft 21 within inner lumen 12 of cannula 11 to discharge markers 14 and 15 from the discharge opening 17 in the cannula. As shown a plurality of short term ultrasonically detectable markers 15 are disposed within the inner lumen 12 distal to the fibrous marker 14. The cannula 11 has a sharp, tissue penetrating distal tip 23 to facilitate advancement through tissue to the target site within the patient. A ramp 24 within the discharge opening 17 of the cannula 11 is provided to guide the markers 14 and 15 out through the discharge opening 17.

The manufacture and use of fibrous marker 14 is schematically illustrated in FIGS. 2A-2F. A felt pad or mat 31 of oxidized, regenerated cellulose about 0.125 to about 0.375 inch (3.2-9.3 mm), preferably about 0.25 inch (6.4 mm) thick is compressed and impregnated with a 10% (Wt.) polyethylene glycol in a 70% isopropyl alcohol solution to a mat about 0.03 to about 0.05 inch (0.76-1.3 mm) thick with a length of about 20 mm. A reduction in thickness of 80% or more may be suitable. The compressed mat 31 is cut up into elongated strips 32 with square or near square transverse cross-sectional shapes. The strips 32 are wrapped in a fabric 33 of oxidized regenerated cellulose about 5 to about 10 mm in width and about 20 mm in length, compressed and impregnated with a 10% PEG dispersion and then dried at elevated temperatures (e.g. about 70° F. to about 150° F.) to a diameter of about 0.065 inch (1.65 mm). The fabric 33 should make at least one, preferably two or more complete wraps about the strip 32. The wrapped and compressed strip may then be cut to a desired length to form the fibrous marker 13. Alternatively, the uncompressed mat 31, the strip 32 and fiber wrap 33 may be provided at the desired length for the fibrous marker 13. A radiographically detectable marker element 34 may be formed of a radiopaque material such as 316L stainless steel or titanium wire 35 (OD about 0.005-0.01 inch, 0.13-0.25 mm) may then be crimped about or embedded in a central portion (or other desired portion) of the marker 14. The fibrous marker 14 is then ready for deployment.

Figures 3, 4:
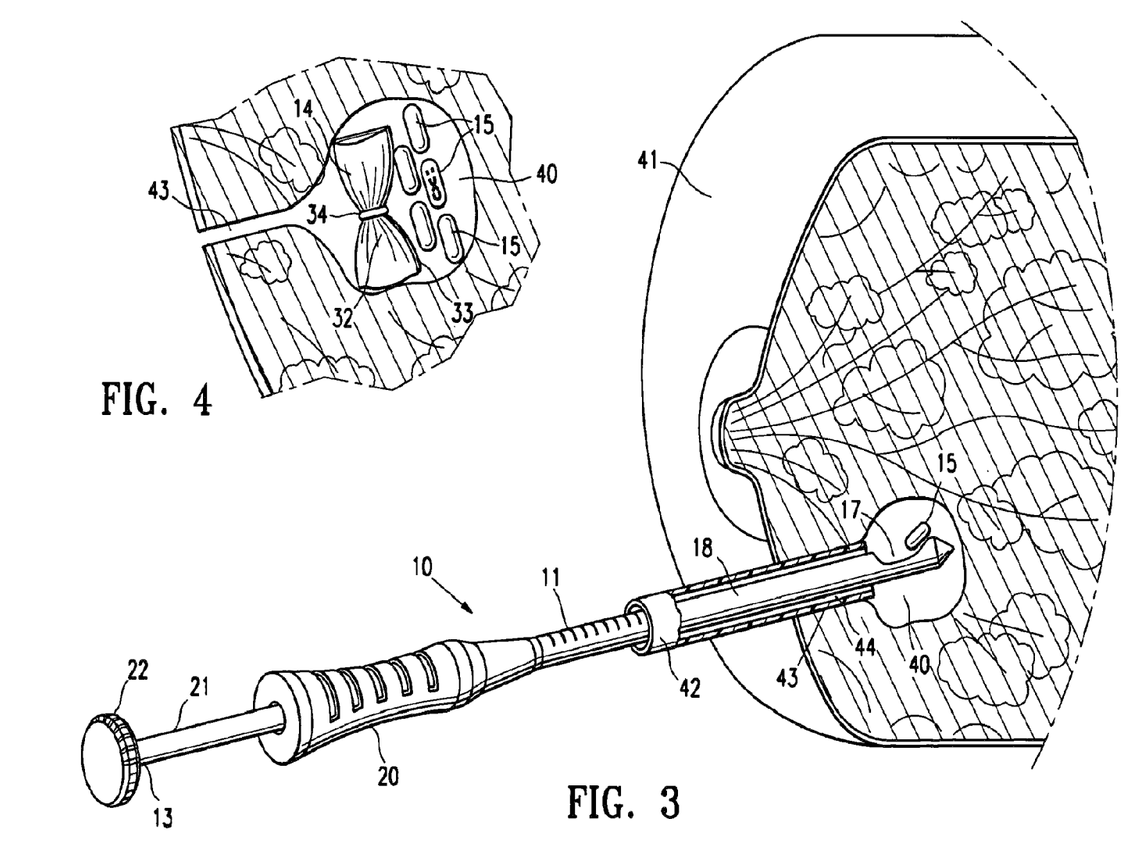
FIG. 3 is a partially cut away, perspective view of a human breast having a biopsy cavity from which a biopsy specimen has been removed, and showing the delivery of a marker to the cavity.
FIG. 4 schematically illustrates the deployment of a plurality of markers, including a marker embodying features of the invention, into a biopsy cavity.

The delivery of the markers into the target site within a human patient is illustrated in FIG. 3. In this particular illustration, the biopsy specimen has already been removed leaving a cavity 40 with the patient's breast 41. A guide cannula 42 remains in the patient from the biopsy procedure. Marker delivery assembly 10 is held by the handle 20 and the shaft 18 thereof containing the markers 14 and 15 is introduced into the inner lumen 44 of the guide cannula 42. The delivery cannula 11 is advanced within the inner lumen 44 until the discharge opening 17 of the delivery cannula is disposed within the cavity 40. The operator then presses the handle 22 on plunger 13 to eject markers 14 and 15 out the discharge opening 17. The pressure on the markers 14 and 15 is sufficient to dislodge the plug 16 which closes off the discharge opening 17. A ramp 24 provided in the discharge opening 17 ensures that the markers 14 and 15 and plug 16 are discharged from the delivery device into the biopsy cavity 40.

Figure 2A:
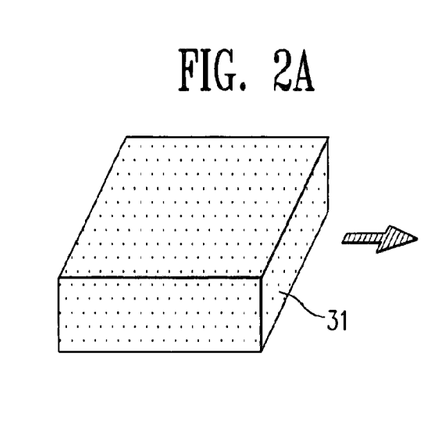
FIGS. 2A-2F schematically illustrate the manufacture and use of a fibrous marker embodying features of the invention.
Figure 2B:
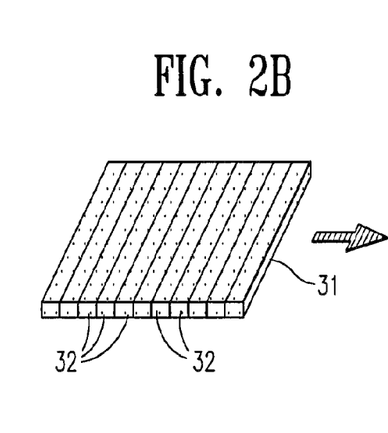
Figure 2C:
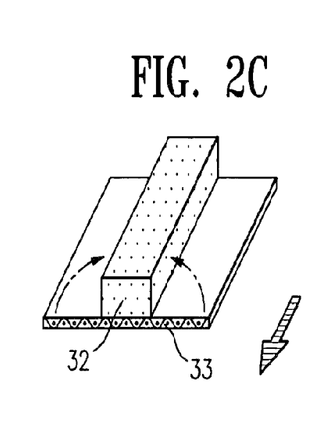
Figure 2D:
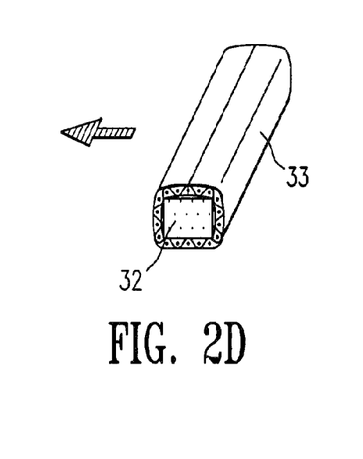
Figure 2E:
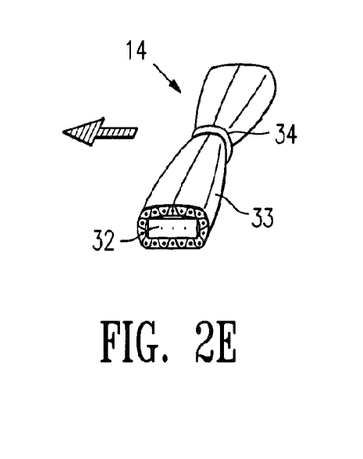
Figure 2F:
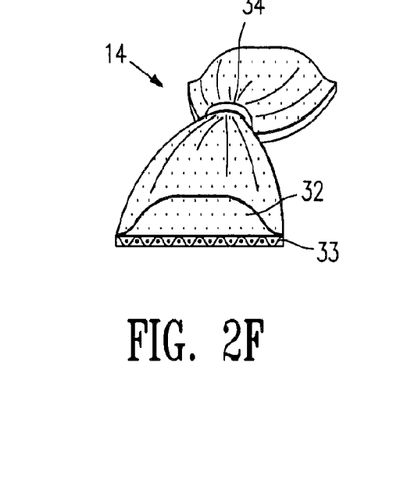

Once the markers 14 and 15 are disposed within the biopsy cavity 40, the fibrous marker 14 begins to swell from the body fluids located in the biopsy cavity. The short term, markers 15 are preferably ejected first and the fibrous marker 14 ejected last. This allows the fibrous marker 14 to swell and unfurl so as to extend across a significant portion of the cavity 40. With a radiographically detectable wire or clip holding a central portion of the marker 14 in a constricted condition, the marker expands into a bow-tie could also place clip/wire to allow full unrolling form rectangular mat shape, as shown in FIG. 4, to center the radiopaque marker element 34 within the cavity 40. This expansion will also tend to block off the accessing passageway 43 leading to the cavity 40 to prevent excursions of the markers 14 or other elements back into the passageway 43 which can cause the physician to miss the biopsy site cavity on subsequent examination. The marker 14 is schematically illustrated in FIG. 2F as having felt layer 32 over the entire surface of fabric layer 33. However, in a clinical setting the layer 32 will cover only a portion of the layer 33.

The fibrous marker is preferably formed of a felt and/or fiber material formed of oxidized regenerated cellulose. However, the fibrous marker may be formed of a bioabsorbable polymer such as polylactic acid, a co-polymer of polylactic acid and glycolic acid, polycaprolactone, collagen and mixtures thereof, including mixtures with oxidized regenerated cellulose. Suitable oxidized, regenerated cellulose includes SURGICEL™ from the Ethicon Division of Johnson & Johnson or other suitably oxidized regenerated cellulose. The fibrous marker may be formed of naturally hemostatic materials such as oxidized, regenerated cellulose or a hemostatic agent such as collagen or gelatin may be incorporated into the fibrous material to provide the hemostasis upon contact with blood. A wide variety of other hemostatic agents may be incorporated into the marker. The thrombus formed by the hemostasis is formed very quickly to fill the cavity at the biopsy site and at least temporarily hold the markers 14 and 15 in position within the cavity. Anesthetic agents to control post procedure pain, chemotherapeutic agents to kill any residual neoplastic tissue, coloring agents (e.g. carbon black and methylene blue) for visual location of the biopsy site, may also be incorporated into the fibrous marker.

The radiopaque marker element is preferably clamped about the exterior of the fibrous material. However, a suitable radiopaque marker may be incorporated or otherwise embedded into the fibrous material to facilitate the location of the marker element by the fibrous marker within the biopsy cavity. The fibrous marker is generally configured to be slidably disposed within the inner lumen of the delivery cannula, and before delivery is about 0.5 mm to about 12 mm, preferably about 1 to about 8 mm in diameter and about 5 to about 30 mm, preferably about 10 to about 25 mm in length. Upon contact with a body fluid or other water based fluid, the length of the fibrous marker remains about the same but the wrapped structure unfolds upon swelling to a width of about 5 to about 25 mm, usually about 10 to about 20 mm. With a radiopaque marker element clamped about a center portion of the wrapped fibrous marker, the fibrous marker expands into a generally bow-tie shape when exposed to body fluids. However, even though secured to the fibrous marker, the radiopaque marker element need not restrict the expansion of the fibrous marker.

The short term marker, which is primarily designed for ultrasound detection over a period of several hours to several months, is preferably formed of a bioabsorbable material such as polylactic acid-glycolic acid copolymer. However, the short term marker may be formed of other bioabsorbable materials including polylactic acid and porcine gelatin. The short term marker materials are processed to include bubbles about 20 to about 1000 micrometers in diameter for ultrasound detection. The bubble formation is preferably formed by the addition of sodium bicarbonate, but air may be physically incorporated while mixing the bioabsorbable material. The life of a particular short term marker may be controlled by the molecular weight of the polymer material from which it is made, with the higher molecular weights providing longer marker life. Suitable short term markers include the GelMark, which is a gelatin based marker, and GelMark Ultra which is a polylactic acid-glycolic acid copolymer based marker, sold by the present assignee. See also U.S. Pat. No. 6,161,034, U.S. Pat. No. 6,427,081, U.S. Pat. No. 6,347,241 and application Ser. No. 09/717,909, filed on Nov. 20, 2000, now U.S. Pat. No. 6,725,083, and application Ser. No. 10/174,401, filed on Jun. 17, 2002, now U.S. Pat. No. 7,651,505, which are incorporated herein by reference in their entirety. The short term markers are configured to be slidably disposed within the inner lumen of the delivery cannula and generally are about 0.5 mm to about 12 mm, preferably about 1 to about 3 mm in diameter, typically about 1.5 mm, and about 1 to about 20 mm, preferably about 2.5 to about 15 mm in length. The short term markers are preferably shorter than the fibrous marker.

The plug used to occlude the discharge opening of the delivery cannula may be formed of the same material as the short term marker and indeed may be employed as a short term marker itself. The plug is preferably formed of or coated with polyethylene glycol which readily hydrates in the presence of body fluids and which causes the plug to swell and occlude the discharge opening. This prevents premature contact between body fluids and the markers within the inner lumen of the delivery device which can cause the markers to swell in the lumen and prevent or retard their deployment to the target site.

An operator may grasp a device handle 20 to guide the device 10 during insertion, and to steady the device 10 during depression of the plunger 13. Insertion of a device 10 results in the placement of at least a portion of the device 10 adjacent a desired location. The device 10, in particular the distal tip 23 and orifice 17 of the device 10, may be guided adjacent a desired location such as a lesion site, or a biopsy cavity, or other internal body site where delivery of a marker 14 is desired.

The short term marker typically should remain in place and be detectable within a patient for a period of at least 2 weeks to have practical clinical value, preferably at least about 6 weeks, and may remain detectable for a time period of up to about 20 weeks, more preferably for a time period of up to about 12 weeks. The fibrous marker should have a life period of short duration, e.g. less than 30 days but the radiographically detectable marker element of the fibrous marker should have a life of at least one year and preferably is permanently radiographically detectable.

While stainless steel and titanium are preferred radiopaque materials, the radiopaque elements may be made of suitable radiopaque materials such as platinum, gold, iridium, tantalum, tungsten, silver, rhodium, nickel, NiTi alloy. MRI contrast agents such as gadolinium and gadolinium compounds, for example, are also suitable for use with plugs and/or markers embodying features of the invention.

Marker delivery devices other than those shown in FIGS. 1A-1C may be employed. Other suitable delivery devices are depicted in U.S. Pat. No. 6,347,241 and application Ser. No. 09/717,909, now U.S. Pat. No. 6,725,083, which have been incorporated herein by reference.

While particular forms of the invention have been illustrated and described herein, it will be apparent that various modifications and improvements can be made to the invention. Moreover, those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action.

All patents and patent applications referred to above are hereby incorporated by reference in their entirety.

What is claimed is:

1. An intracorporeal marker comprising a fibrous unitary marker body having bioabsorbable fibers compressed into a compressed configuration, and bound in the compressed configuration by a polymer binding agent.

2. The intracorporeal marker of claim 1, wherein a radiopaque marker element is incorporated into the fibrous unitary marker body.

3. The intracorporeal marker of claim 2, wherein the radiopaque marker element is disposed about the fibrous unitary marker body.

4. The intracorporeal marker of claim 1, wherein the bioabsorbable fibers comprise a bioabsorbable material selected from the group consisting of cellulose, polylactic acid, a copolymer of polylactic acid and glycolic acid, and polycaprolactone.

5. The intracorporeal marker of claim 4, wherein the cellulose is oxidized, regenerated cellulose.

6. The intracorporeal marker of claim 1, wherein the bioabsorbable fibers comprise a woven fabric.

7. The intracorporeal marker of claim 1, wherein the bioabsorbable fibers comprise a felt fabric.

8. The intracorporeal marker of claim 1, wherein the polymer binding agent comprises one or more water soluble polymers selected from the group consisting of polyvinyl alcohol, polyethylene glycol, polyvinyl pyrollidone.

9. The intracorporeal marker of claim 1, wherein the fibrous unitary marker body includes at least one bioactive component selected from the group consisting of therapeutic and diagnostic agents incorporated therein.

10. The intracorporeal marker of claim 1, wherein the bioabsorbable fibers comprise a material selected from the group consisting of polylactic acid, a co-polymer of polylactic acid and glycolic acid, polycaprolactone, collagen and mixtures thereof, including mixtures with oxidized cellulose.

11. The intracorporeal marker of claim 1, further comprising a constricting member configured to hold a portion of the fibrous unitary marker body to prevent an expansion of the portion upon contact with a water-based fluid.

12. The intracorporeal marker of claim 11, wherein the constricting member is a radiographically detectable marker element.

13. The intracorporeal marker of claim 1, wherein the fibrous unitary marker body comprises a core of bioabsorbable felt surrounded by a bioabsorbable fabric jacket.

14. The intracorporeal marker of claim 1, wherein a radiopaque marker element is incorporated into the fibrous unitary marker body.

15. An intracorporeal marker delivery device, comprising:
a delivery cannula which has a distal tip, an inner lumen and a discharge opening in communication with the inner lumen; and
a fibrous unitary marker body comprising bioabsorbable fibers which is compressed into a compressed configuration and bound in the compressed configuration by a binding agent prior to insertion into the inner lumen of the delivery cannula, the fibrous unitary marker body being slidably disposed within and pushable through the inner lumen of the elongated delivery cannula proximal to the discharge opening.

16. The intracorporeal marker delivery device of claim 15, wherein the bioabsorbable fibers expand upon contact with body fluid or other water based fluid.

17. The intracorporeal marker delivery device of claim 15, further comprising a short term ultrasonically detectable marker slidably disposed within the inner lumen of the delivery cannula proximal to the discharge opening.

18. The intracorporeal marker delivery device of claim 15, wherein the discharge opening of the delivery cannula is occluded by a bioabsorbable plug to prevent the premature contact of the fibrous unitary marker body within the inner lumen with body fluids at a tissue site.

19. An intracorporeal marker comprising a fibrous unitary marker body having bioabsorbable fibers compressed into a compressed configuration, and bound in the compressed configuration by a binding agent.

20. The intracorporeal marker of claim 19, wherein the fibrous unitary marker body comprises a core of bioabsorbable felt surrounded by a bioabsorbable fabric jacket.

* * * * *